US008546332B2

(12) United States Patent
Lenting et al.

(10) Patent No.: US 8,546,332 B2
(45) **Date of Patent: *Oct. 1, 2013**

(54) FACTOR VIII POLYPEPTIDE HAVING FACTOR VIII:C ACTIVITY

(75) Inventors: Petrus Johannes Lenting, Amsterdam (NL); Jan Aart Van Mourik, Badhoevedorp (NL); Koenraad Mertens, Leiden (NL); Hans Pannekoek, Aalsmeer (NL); Peter Turecek, Klosterneuburg (AT); Hans-Peter Schwarz, Vienna (AT); Friedrich Scheiflinger, Vienna (AT)

(73) Assignee: Stichting Sanquin Bloedvoorziening, Amsterdan (NL)

( * ) Notice: Subject to any disclaimer, the term of this patent is extended or adjusted under 35 U.S.C. 154(b) by 656 days.

This patent is subject to a terminal disclaimer.

(21) Appl. No.: 12/388,665

(22) Filed: Feb. 19, 2009

(65) Prior Publication Data

US 2011/0118188 A1 May 19, 2011

Related U.S. Application Data

(63) Continuation of application No. 10/986,281, filed on Nov. 12, 2004, now Pat. No. 7,544,660, which is a continuation of application No. 09/831,679, filed on May 10, 2001, now Pat. No. 6,919,311, which is a continuation of application No. PCT/AT99/00272, filed on Nov. 10, 1999.

(30) Foreign Application Priority Data

Nov. 10, 1998 (AT) ........................................ 1872/98

(51) Int. Cl.
*A61K 38/37* (2006.01)
*A61K 38/00* (2006.01)

(52) U.S. Cl.
USPC ....... 514/14.1; 514/13.7; 514/287.1; 530/350

(58) Field of Classification Search
None
See application file for complete search history.

(56) References Cited

U.S. PATENT DOCUMENTS

| | | | | |
|---|---|---|---|---|
| 5,859,204 | A * | 1/1999 | Lollar | 530/383 |
| 2005/0074836 | A1* | 4/2005 | Lenting et al. | 435/69.1 |

OTHER PUBLICATIONS

Pemberton et al. (1997) A molecular model for the triplicated A domains of human factor VIII based on the crystal structure of human ceruloplasmin, Blood. vol. 89, No. 7, pp. 2413-2421.*
Healey et al. (1996) The cDNA and derived amino acid sequence of porcine factor VIII, Blood, vol. 88, No. 11, pp. 4209-4214.*

* cited by examiner

*Primary Examiner* — Karen Cochrane Carlson
*Assistant Examiner* — Samuel Liu
(74) *Attorney, Agent, or Firm* — Perkins Coie LLP

(57) ABSTRACT

Factor VIII polypeptides having FVIII:C activity that contain modifications in the A3 and/or C1 and/or C2 domains of the sequence of the light chain of Factor VIII, characterized by the binding affinity to low density lipoprotein receptor protein, and methods for producing the same.

8 Claims, 9 Drawing Sheets

FACTOR VIII POLYPEPTIDE HAVING FACTOR VIII:C ACTIVITY

CROSS REFERENCE TO RELATED APPLICATIONS

This application is a continuation of U.S. application Ser. No. 10/986,281 filed Nov. 12, 2004, now U.S. Pat. No. 7,544, 660, which is a continuation of U.S. application Ser. No. 09/831,679 filed May 10, 2001, now U.S. Pat. No. 6,919,311, which is a continuation of PCT/AT99/00272 filed Nov. 10, 1999, the entireties of which are hereby incorporated by reference.

REFERENCE TO SEQUENCE LISTING

A Sequence Listing in computer readable format is included herewith.

FIELD OF INVENTION

The present invention relates to modified Factor VIII (FVIII) polypeptides having FVIII:C activity and containing modifications in the A3 and/or C1 and/or C2 domains of the sequence of the light chain of Factor VIII. Furthermore, the present invention relates to nucleic acid molecules encoding such modified Factor VIII polypeptides, vectors and host cells containing said nucleic acid molecules, and compositions containing said Factor VIII polypeptide for use in the treatment of hemorrhagenic disturbances.

BACKGROUND OF THE INVENTION

Hemostasis involves the interaction of various hemostatic reaction routes finally leading to thrombus formation. Thrombi are deposits of blood components on the surface of the vascular wall that mainly consist of aggregated blood platelets and insoluble cross-linked fibrin. Fibrin formation is the result of the restricted proteolysis of fibrinogen by thrombin, a coagulation enzyme. Thrombin is the end product of the coagulation cascade, a succession of zymogen activations occurring on the surfaces of activated blood platelets and leucocytes, and a variety of vascular cells (for a survey, cf. K. G. Mann et al., Blood, 1990, Vol. 76, pp. 1-16).

A key function in the coagulation cascade resides in the activation of Factor X by the complex of activated Factor IX (Factor IXa) and activated Factor VIII (Factor VIIIa). A deficiency or a dysfunction of the components of this complex is associated with the blood disease known as hemophilia (J. E. Sadler & E. W. Davie: Hemophilia A, Hemophilia B, and von Willebrand's Disease, in G. Stamatoyannopoulos et al., (Eds.): The molecular basis of blood diseases. W.B. Saunders Co., Philadelphia, 1987, pp. 576-602). Hemophilia A is related to a deficiency of Factor VIII activity, whereas Hemophilia B is related to a Factor IX deficiency. Current treatment consists of a replacement therapy using pharmaceutical preparations comprised of the normal coagulation factor. Of these thrombopathies, Hemophilia A occurs more frequently, affecting approximately one out of 10,000 men. Replacement therapy in Hemophilia A patients involves the repeated administration of preparations containing normal Factor VIII by intravenous infusion. The interval between the infusions is a function of the degradation of the Factor VIII activity in blood circulation. The half-life of the Factor VIII activity after an infusion differs from one individual to another, ranging from 10 to 30 hours. Thus, a prophylactic therapy requires an infusion every two to three days. This constitutes a heavy load on the life of hemophilic patients, in particular, if the venous access has become difficult due to local citratization following frequent needle punctures for intravenous infusions.

It would be particularly advantageous if the frequency of infusions could be lowered by using Factor VIII having extended half-lives. The half-life of Factor VIII may be extended by interfering with the mechanism of Factor VIII degradation (clearance), for instance, by reducing the affinity of Factor VIII to receptors that are essential to its clearance, either directly by modifying Factor VIII on its binding site(s) for the clearance receptors concerned, or indirectly by using compounds interfering with the interaction of Factor VIII with those receptors. However, the design of such agents has so far been impeded by not knowing the Factor VIII clearance mechanism, the cell receptors involved in this process, and the molecular sites involved in the Factor VIII receptor interaction.

There is limited knowledge in the molecular field as to the clearance mechanism of Factor VIII. The Factor VIII protein is synthesized as a single chain polypeptide comprising 2332 amino acids and having the typical domain structure A1-A2-B-A3-C1-C2 (G. A. Vehar et al., Nature, Vol. 312, 1984, pp. 337-342; J J. Toole et al., Nature, Vol., 312, 1984, 342-347). Factor VIII enters the blood circulation as a heterodimeric complex of heavy and light chains as a result of intracellular endoproteolytic processing. The light chain comprises the amino acid residues 1649-2332 and contains the A3-C1-C2 domains. The heavy chain contains the domains A1-A2-B (residues 1-1648) and is heterogenic due to the limited proteolysis in a number of positions within the B domain. The Factor VIII heterodimer has no biological activity, but the heterodimer becomes active as a cofactor of the enzyme Factor IXa after proteolytic activation by thrombin or Factor Xa. Proteolysis affects both the heavy chain and the light chain of Factor VIII (M. J. S. H. Donath et al., J. Biol. Chem., Vol. 270, 1995, pp. 3648-3655), leading to the cleavage of an amino-terminal fragment from the light chain and a break of domain connection sites within the heavy chain (between domains A1-A2 and A2-B). The activated cofactor, Factor VIIIa, is a heterotrimer comprised of the A1 domain, the A2 domain and the light chain including domains A3-C1-C2.

It is well known in the art that the half-life of the non-activated Factor VIII heterodimer strongly depends on the presence of von Willebrand Factor, which exhibits a strong affinity to Factor VIII (yet not to Factor VIIIa) and serves as a carrier protein (J. E. Sadler and E. W. Davie: Hemophilia A, Hemophilia B and von Willebrand's disease, in G. Stamatoynnopoulos et al. (Eds.): The molecular basis of blood diseases. W.B. Saunders Co., Philadelphia, 1987, pp. 576-602). It is known that patients suffering from von Willebrand's disease type 3, who do not have a detectable von Willebrand Factor in their blood circulation, also suffer from a secondary Factor VIII deficiency. In addition, the half-life of intravenously administered Factor VIII in those patients is 2 to 4 hours, which is considerably shorter than the 10 to 30 hours observed in Hemophilia A patients.

From these findings results that Factor VIII tends to a rapid clearance from the blood circulation and that this process is to some extent inhibited by complexation with its natural carrier, von Willebrand Factor. Nevertheless, its half-life remains undesirably short.

Recently, it has been indicated in a preliminary report that Factor VIII activated by thrombin binds to low density lipoprotein receptor protein ("LRP") (A. Yakhyaev et al., Blood, Vol. 90 (Suppl. 1), 1997, 126-I (Abstract). This abstract describes the cell absorption and the degradation of Factor VIII fragments activated by thrombin and reports that the A2 domain, unlike the two other subunits of the Factor VIIIa heterotrimer, interacts with cell-bound LRP. The authors have suggested that binding of the A2 domain to LRP further destabilizes the loose interaction of the A2 domain in the Factor VIIIa heterotrimer and thereby downwardly regulating Factor VIIIa activity.

It is known that LRP is one of the receptors that are involved in the clearance of various proteins. LRP in this field is also known as the alpha2-macroglobulin receptor, belonging to the family of low density lipoprotein (LDL) receptors. It is comprised of two non-covalently connected polypeptide chains: an alpha chain (515 kd) and a β-chain (85 kd) [for a review refer to D. K. Strickland et al., *FASEB J* Vol. 9, 1995, pp. 890-898]. LRP is. a multi-ligand receptor for lipoprotein and proteinase catabolism. The β-chain includes a transmembrane domain and a short cytoplasmatic tail which is essential to endocytosis. The alpha chain functions as a large ectodomain and includes three types of repeats: epidermal growth factor-like domains, Tyr-Trp-Thr-Asp sequences and LDL receptor class A domains. These class A domains are present in four separate clusters, clusters I (2 domains), II (8 domains), III (20 domains) and IV (11 domains). It has been shown that these clusters are involved in ligand binding. LRP is expressed in a plurality of tissues such as the placenta, lungs, brain, and liver. In the liver, LRP is present on parenchyma cells and Kupffer cells. Moreover, LRP is expressed in a plurality of cell types such as fibroblasts, smooth muscle cells, Leydig cells, Sertoli cells, and monocytes. The differentiation from monocytes to macrophages is associated with a drastic Increase in LRP expression. Finally, LRP is expressed also in cell types such as ape kidney cells (COS) or Chinese hamster ovary cells (CHO) (D. J. FitzGerald et al., J. Cell Biol. Vol. 129, 1995, pp. 1533-1541), which are both frequently used to express mammalian proteins including Factor VIII (R. J. Kaufman et al., Blood Coag. Fibrinol. Vol. 8 (Suppl. 2), 1997, pp. 3-14).

LRP is involved in the clearance of a diversity of ligands including proteases, inhibitors of the Kunitz type, protease serpin complexes, Upases and lipoproteins, which suggests that LRP plays an essential role in various physiological and pathophysiological clearance processes (Narita et al., Blood, Vol. 2, pp. 555-560, 1998; Orth et al., Proc. Natl. Acad. Sci., Vol. 89, pp. 7422-7426, 1992; Kounnas et al., J. Biol. Chem., Vol. 271, pp. 6523-6529, 1996). LRP's physiological importance goes back to the finding that LRP knock-out mice do not survive the embryonic stage (Herz, J. Curr. Opin. Lipidol. Vol. 4, 1993, pp. 107-113). LRP secretion may be complicated by LRP interacting with multiple ligands. Within the cell, LRP is, however, associated with its chaperone protein, the receptor-associated protein (RAP). If bound to RAP, LRP cannot interact with any of its known ligands (Herz et al., J. Biol. Chem., Vol. 266, pp. 21232-21238, 1991).

The interaction of LRP with its natural ligands may be effectively blocked by soluble LRP fragments. These fragments may be obtained by various methods known in the art, including recombinant techniques, and as such provide access to effective LRP antagonists (I. R. Horn, J. Biol. Chem., Vol. 272, 1997, pp. 13608-13613; B. Vash et al., Blood, Vol. 92, 1998, pp. 3277-3285).

In view of the typical role of LRP in the clearance of proteases, inhibitors and protease inhibitor complexes, it is to be noted that LRP also binds the activated non-enzymatic cofactor Factor VIIIa (A. Yakhyaev et al., Blood Vol. 90 (Suppl. 1), 1997, 126-1 (Abstract)). While that disclosure suggests LRP's role in the regulation of Factor VIIIa, it does not give any hint as to its role in the regulation of non-activated heterodimeric Factor VIII, although this would be of potential interest for the clearance of Factor VIII from the blood circulation—and hence the half-life of Factor VIII.

There have been several prior art attempts to enhance the pharmacokinetic profile of Factor VIII, including modifications in various regions of Factor VIII polypeptides.

WO 87/07144 describes various modifications of proteolytic interfaces comprising arginine and lysine residues, reducing the instability of the molecules for a specific protease-catalyzed cleavage, for instance the Factor VIIIa interface between Arg 1721 and Ala 1722.

WO 95/18827, WO 95/18828 and WO 95/18829 describe Factor VIII derivatives with modifications in the A2 region of the heavy chain.

WO 97/03193 discloses Factor VIII polypeptide analogs in which the modifications comprise alterations of the metal binding properties of the molecule.

WO 97/03195 describes Factor VIII:C polypeptide analogs in which modifications are provided on one or several amino acid residues adjacent an Arg residue.

EP-0 808 901 describes the construction of Factor VIII variants including at least one mutation in at least one immunodominant region of Factor VIII and the use of these Factor VIII variants in the treatment of patients with Factor VIII inhibitors. Those modifications do not result in an extended half-life or enhanced stability of the Factor VIII variant, neither in vivo nor in vitro.

In light of the prior art, none of the documents suggests that a modification in the light chain of Factor VIII will lead to a modified binding affinity relative to a cell receptor and, consequently, to a reduced clearance of the Factor VIII protein and an extended half-life and an enhanced stability of Factor VIII.

BRIEF SUMMARY OF THE INVENTION

Therefore, it is an object of the present invention to provide a Factor VIII polypeptide having Factor VIH:C activity, which exhibits an extended half-life and/or an enhanced stability of the Factor VIII protein in vivo and/or in vitro. Accordingly, the present invention provides a Factor VIII polypeptide containing a modification in the light chain of the molecule, which influences the binding affinity to low density lipoprotein receptor protein (LRP).

In a preferred embodiment of the invention, the Factor VIII polypeptide modification is contained in the A3 domain, between amino acid sequence (AS) 1690 and 2032, in the C1 domain, between AS 2033 and 2172, and/or in the C2 domain of the light chain, between AS 2173 and 2332 (all amino acid numerations made in the instant application in respect to the Factor VIII sequence refer to the numeration of Vehar et al. (Nature, Vol: 312, 1984, pp. 337-342), the entire contents of which are hereby incorporated by reference.

The modification in the A3 domain is contained, in particular, between AS 1722 (Met) and 1725 (Gly), AS 1743 (Phe) and 1749 (Arg), AS 1888 (Ser) and 1919 (His), As 1942 (Trp) and 1947 (Met) and/or AS 1959 (Ser) and 1974 (Ala).

In another embodiment of the present invention, the modification in the C1 domain is contained between AS 2037 (He) and 2062 (Trp), AS 2108 (Asp) and 2118 (Asn) and/or AS 2154 (Thr) and 2158 (He). In a more preferred manner, the modification is contained between AS 2112 (Trp) and 2115 (Tyr).

Preferably, the modification is contained between AS 2209 (Arg) and 2234 (Phe) and/or AS 2269 (His) and 2281 (Lys) of the C2 domain.

In an even more preferred manner, the modification is contained between AS 2211 (His) and 2230 (Leu).

DETAILED DESCRIPTION

Figure 1:
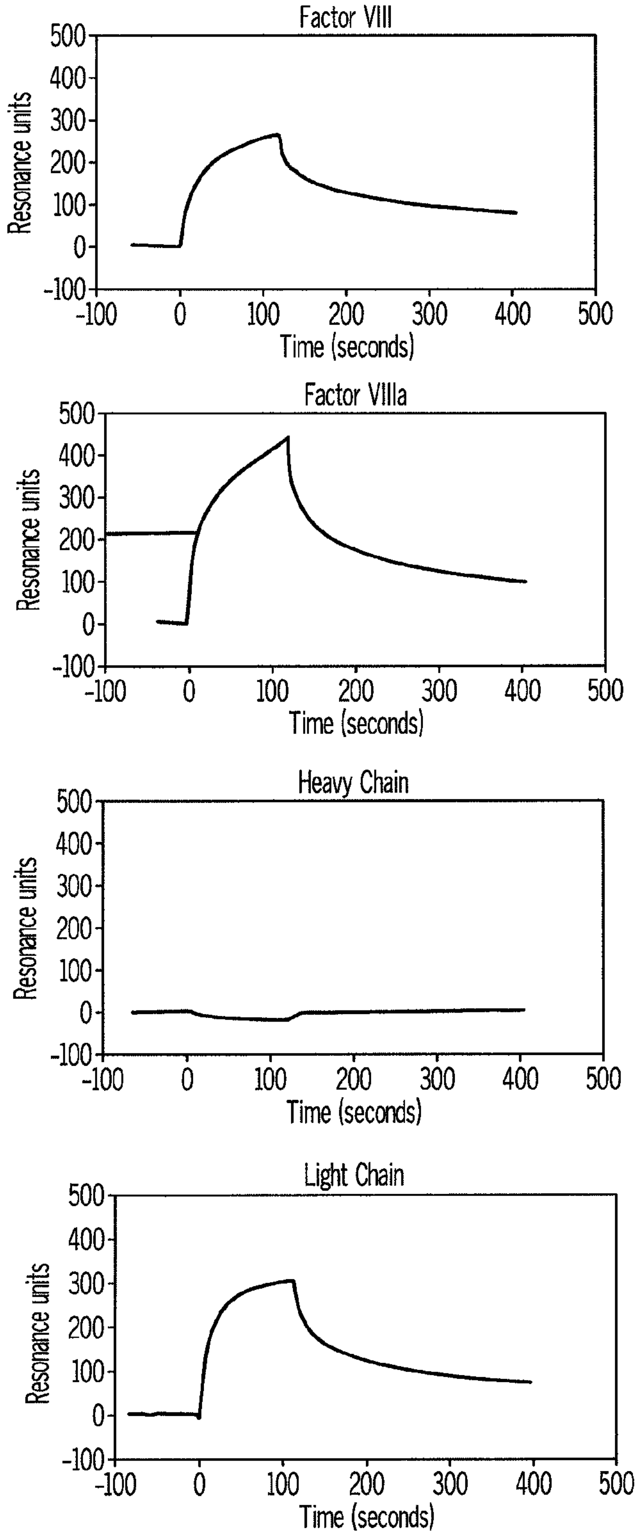
FIG. 1 illustrates the interaction between Factor VIII (Table A), thrombin-activated Factor VIII (Factor VIIIa, Table B), the heavy chain of Factor VIII (Table C) or the light chain of Factor VIII. (Table D), respectively, and immobilized LRP using surface plasmon resonance analysis. Details are provided in Example I. A comparison of Tables A-D shows that Factor VIII, thrombin-activated Factor VIII, the light chain of Factor VIII, but not the heavy chain of Factor VIII, interact efficiently with LRP.

Within the context of the present invention, it has been found that the inhibition of LRP by its antagonist, RAP, results in Factor VIII light chain accumulation in the medium. This proves that the cellular absorption of the Factor VIII heterodimer encompasses an LRP-dependent mechanism.

Surprisingly, it has been shown that a modification in the light chain of the Factor VIM polypeptide has a similar effect, i.e., an increased half-life and stability of the Factor VIII protein. Due to Factor VIII molecule modification, the binding affinity to LRP decreases, which inhibits the rapid clearance of the protein. This finding offers new options for an enhanced treatment of coagulation disturbances, which might be necessary in the preparation of Factor VIII compositions.

Due to the modification contained in the Factor VIII polypeptide, the increase in the in vivo and in vitro half-lives of the Factor VIII molecule according to the present invention may be at least 10%, preferably 25%, more preferably 60%, still more preferably 90%, as compared to the wild-type Factor VIII protein.

Factor VIII polypeptides or Factor VIII variants made in accordance with the teachings of the present invention exert their beneficial effects because they constitute interactive regions (exosites) located on the subunits of the Factor VIII heterodimer, in particular, on the light chain of Factor VIII (domains A3-C1-C2). The term exosite is used herein in its broadest sense, relating to relatively hydrophilic moieties of the protein, which are directed primarily at the surface of the Factor VIII molecule (Kyte and Doolittle, J. Mol. Bio!., Vol. 57, pp. 105-132, 1982).

Although the process of Kyte and Doolittle operates according to principles already acknowledged in this field, based on the Factor VIII sequence as previously published, no attention has so far been practically paid to these hydrophilic exosites. The exosite at amino acid sequence (AS) Ser 1784 to Asp 1831, for instance, includes the binding region of Factor IX, which has already been described in the literature (AS 1801 to 1823, P. J. Lenting et al., J. Biol. Chem., Vol. 271, pp. 1935-1940). This clearly demonstrates the relevance of the hydropathy plots used to identify exosites. The term "binding site" herein refers to a typical sequence pattern of amino acids, including their natural and synthetic analogs which meet the minimum requirements for the binding of non-activated Factor VIII to LRP.

In a first group of preferred embodiments of the invention, the polypeptide contains a modifcation in one or several of the exosites within the sequence of the Factor VIII polypeptide, preferably of the light chain of Factor VIII, and more preferably of the C2 domain of Factor VIII. In addition, these polypeptides preferably are derived from the sequence of human Factor VIII, although the invention comprises binding sites that are based on Factor VIII exosites of any desired mammalian species.

Modification may be carried out for instance, by directed in vitro mutagenesis, PCR, or other prior art methods of bioengineering suitable for the specific alteration of a DNA sequence aimed at the directed replacement of amino acids (Current Protocols in Molecular Biology, Vol. 1, Chapt. 8 (Ausubel et al., Eds., J. Wiley and Sons, 1989 & Suppl. 1990-93); Protein Engineering (Oxender & Fox Eds., A. Liss, Inc., 1987)). This modification may be comprised of a mutation, deletion, or insertion in the Factor VIII light chain region.

Furthermore, the present invention provides the nucleic acids that encodes each of the modified Factor VIII proteins encompassed by the present invention. The nucleic acids may be DNA or RNA. The nucleic acids are contained in an expression vector that provides the elements which are suitable for the expression of this DNA or RNA. For instance, the expression vector may comprise, in the transcription direction, a transcriptional regulation region and a translational initiation region which are functional in a host cell, a DNA sequence encoding the FVIII polynucleotide of the present invention, and translational and transcriptional termination regions that are functional in this host cell, and the expression of this nucleic sequence being regulated by the initiation and termination regions. The expression vector also may contain elements for the replication of this DNA or RNA. The expression vector may be a DNA or RNA vector. Examples of DNA expression vectors include pBPV, pSVL, pRc/CMV, pRc/RSV, myogenic vector systems as disclosed in (WO 93/09236) or vectors originating from virus systems, for instance, from vaccinia virus, adenoviruses, adeno-associated virus, herpes viruses, retroviruses or baculoviruses. Examples of RNA expression vectors include vectors originating from RNA viruses such as retroviruses or flaviviruses.

The nucleic acids, DNA, and RNA may be chemically modified for those specific applications in genetic therapy where nucleic acids are injected into the organ of a mammal. Chemical modifications may include modifications to protect the nucleic acid against nuclease digestion, for instance, by stabilizing its skeleton or termini.

The expression vector which contains the nucleic acid encoding the modified Factor VIII polypeptide according to the present invention may be used to transform host cells which will then produce this polypeptide. The transformed host cells may be grown in a cell culture system in order to produce this polypeptide in vitro. The host cells can segregate the modified Factor VIII polypeptide into the cell culture medium, from which it can be purified. The host cells also can keep the modified Factor VIII polypeptide within their cell walls, and the hybrid protein may be produced from the host cells.

Mammalian body cells such as fibroblasts, keratinocytes, hematopoietic cells, hepatocytes, or myoblasts may be used as host cells. The host cells are transformed in vitro by an expression vector system that carries a nucleic acid made in accordance with the teachings of the present invention and are reimplanted into the mammal. The Factor VIII polypeptide encoded by this nucleic acid is synthesized in vivo by these cells, and they will exhibit a desired biological activity in the mammal. According to one embodiment of the present invention, the mammal is a human patient suffering from hemophilia.

The nucleic acid sequence encoding the modified Factor VIII polypeptide made in accordance with the teachings of the present invention also may be used to create transgenic animals expressing these modified Factor VIII polypeptide proteins in vivo. In one embodiment of this specific application, the transgenic animals are able to produce the Factor VIII polypeptide in endogenous glands such as mammary glands, from which these proteins can be separated. For example, Factor VIII proteins produced in the mammary glands can be separated into the milk of the animals to produce these proteins/The animals may include, but are not limited to, mice, cattle, pigs, goats, sheep, rabbits or any other economically useful animal.

Furthermore, the expression vector which contains the nucleic acid encoding for any Factor VIII polypeptide encompassed by the present invention may be administered to mammals without previous in vitro transformation in host cells. The practical background for this type of genetic therapy is disclosed in several patent applications such as WO 90/11092. The expression vector containing this nucleic acid sequence is mixed with a suitable carrier, such as a physiological buffer solution, and injected into an organ, preferably a skeletal muscle, the skin, or the liver of a mammal. The mammal preferably is a human being and, more preferably, is a subject suffering from a genetic defect and, most preferably, a subject suffering from a blood coagulation disturbance. In a particular embodiment, the mammal is a human patient suffering from hemophilia, and the nucleic acid contained in the expression vector encodes the modified Factor VIII polypeptide, as described.

It is advantageous that the modified Factor VIII protein according to the present invention has a Factor VIII procoagulant activity of at least 50%, more preferably at least 80%, in particular at least 100%, of the Factor VIII procoagulant activity of a Factor VIII protein without the modification that leads to a reduced binding affinity to LRP, for instance, of a commercially available Factor VIII preparation based on recombinant or plasmatic Factor VIII:C.

The evaluation of the Factor VIII procoagulant activity may be effected by means of any suitable test, in particular those tests which are routinely carried out in the investigation of Factor VIII samples such as the one-stage clot test as described in Mikaelsson and Oswaldson, Scand. J. Haematol. Suppl. 33, pp. 79-86, 1984, or a chromogenic test such as Factor VIII IMMUNOCHROM (Immuno).

The Factor VIII activity also may be determined by measuring the capability of Factor VIII to function as a cofactor to Factor IXa in the conversion of Factor X to Factor Xa, using a chromogenic substrate for Factor Xa (Coatest Factor VIII, Chromogenix, Moelndal, Sweden). In addition, other tests that serve to determine the amount of Factor VIII activity in a sample may be used to test the Factor VIII activity of the modified proteins described in the present invention.

The actual test whether any of the newly modified Factor VIII proteins exhibits a defined percentage of Factor VIII procoagulant activity is preferably carried out in parallel with a test on the same Factor VIII molecule without modification in the LRP binding domain (e.g., Factor VIII wild type or a fully active Factor VIII with a deleted B domain). A calibrated test of the mutant Factor VIII molecule enables the examination of the relative procoagulant activity (the percentage of the activity as compared to a 100% activity of the wild type or of Factor VIII including a B domain deletion) without the risk of an error on account of medium factors. Since the results of in vitro tests for Factor VIII procoagulant activity are often influenced by errors that are due to the artificial nature of the same, the two properties preferably are assayed also by in vivo or ex vivo tests in order to obtain more reliable results in respect to activity values.

Like the in vitro tests, parallel testing of the Factor VIII molecule without modification is also preferred if in vivo tests are carried out. Animal models suitable for the evaluation of the Factor VIII:C activity are described in WO 95/01570 and EP 0 747 060.

A preparation made in accordance with the teachings of the present invention may be provided as a pharmaceutical preparation comprising a modified Factor VIII polypeptide either as a single-component preparation or combined with other components, as a multi-component system. In one embodiment, the Factor VIII proteins or the modified Factor VIII molecules made in accordance with the teachings of the present invention may be combined with one or several polypeptides such as RAP that selectively inhibit the binding and internalization of Factor VIII by low density lipoprotein receptor-related proteins (LRP).

The present invention also contemplates a composition comprising a Factor VIII molecule and one or several polypeptides antagonistically interfering with the interaction between Factor VIII and LRP resulting in the selective inhibition of the binding and internalization of Factor VIII by LRP. Preferably, the polypeptide is RAP or a soluble LRP fragment having an antagonistic effect. Preferably, the soluble LRP fragment binds to Factor VIM in the Factor VIII-LRP binding region.

These preparations may be used as active components of pharmaceutical compositions for the treatment of patients suffering from genetic disturbances, preferably coagulation disturbances, and most preferably hemophilia, for instance hemophilia A. Moreover, these compounds may be used as active components of pharmaceutical compositions for the treatment of patients suffering from temporary disturbances of their thrombotic or fibrinolytic systems that may occur before, during, or after an operation.

In accordance with the present invention, a pharmaceutical composition is intended for the treatment to mammals, preferably humans. When producing the pharmaceutical product of the present invention, compounds of the present invention, modified Factor VIII polypeptides, nucleic acids encoding the same, or the transformed cells capable of in vivo expression of Factor VIII polypeptides are mixed with physiologically acceptable carriers.

The compositions disclosed in the present invention may be formulated for administration in any suitable way, and the invention also encompasses pharmaceutical compositions containing a therapeutically effective amount of Factor VIII. The compositions of the present invention may be formulated in a conventional manner using one or several pharmaceutically acceptable carriers or excipients. Suitable carriers include, but are not limited to, diluents or fillers, sterile aqueous media and various nontoxic organic solvents. The compositions may be formulated in the form of powders, aqueous suspensions or solutions, injectable solutions and the like. Suitable dosage forms will be readily identified by the skilled artisan.

According to the methods of the present invention, treatments for coagulation disturbances should be carried out using a dosage scheme that will guarantee the maximum therapeutic response until improvement has been reached and a subsequent effective minimum dosage amount that offers a suitable protection against bleeding. The dosage for intravenous administration may range between about 10 and 300 IU/kg body weight, preferably between about 10 and 100 IU/kg body weight, and more preferably between 20 and 40 IU/kg body weight. A suitable dosage may also depend on the patient's age, general health, or other factors that may influence the response to the drug. The drug may be administered by continuous infusion or at regular intervals in order to keep the therapeutic effect on the desired level.

Another aspect of the invention relates to a method for producing modified Factor VIII molecules, which contain a modification in the light chain. The sequence encoding the modified Factor VIII molecule is inserted in a suitable expression system such as an expression vector, and suitable cells are transfected with the recombinant DNA. Preferably, permanent cell lines expressing the modified Factor VIII are established. The cells are grown under conditions that are optimal for gene expression, and modified Factor VIII is isolated, either from a cell culture extract or from the cell culture supernatant. The recombinant molecule may be further purified by means of any known chromatographic methods such as anion or cation exchange chromatography, affinity or immunoaffinity chromatography, or a combination thereof.

Modified Factor VIII is preferably produced by recombinant expression. It may be produced recombinantly by means of any usual expression system such as, but not limited to, permanent cell lines or viral expression systems. Permanent cell lines are produced by the stable integration of foreign DNA into the host cell genome of, for instance, vero, MRC5, CHO (Chinese Hamster Ovary), BHK (baby hamster kidney), 293, Sk-Hep1 cells, in particular hepatic and renal cells, fibroblasts, keratinocytes or myoblasts, hepatocytes or stem cells, hematopoietic stem cells, or by an episomal vector derived, for instance, from papilloma virus. Virus expression systems such as vaccinia virus, baculovirus or retrovirus systems may likewise be used. Generally, vero, MRC5, CHO, BHK, 293, Sk-Hep1, glandular, hepatic and renal cells are used as cell lines. Eukaryotic expression systems that may be used include yeast cells, endogenous glandular cells (e.g., glands of transgenic animals) and also other types of cells. Naturally, transgenic animals may also be used for the expression of the polypeptides of the present invention or derivatives thereof. CHO-DHFR cells have proved to be particularly suitable for the expression of recombinant proteins (Urlaub et al., Proc. Natl. Acad. Sci., U.S.A., Vol. 77, pp. 4216-4220, 1980).

Prokaryotic expression systems may also be used for the recombinant production of modified Factor VIII made in accordance with the teachings of the present invention. Systems enabling an expression in *E. coli* or *B. subtilis* are particularly suited.

The Factor VIII polypeptide of the present invention is expressed in the respective expression system under the control of a suitable promoter. Any of the known promoters such as SV40, CMV (cytomegalovirus), RSV (respiratory syncytial virus), HSV (herpes simplex virus), EBV (Epstein Barr virus), p-actin, hGH (human growth hormone) or inducible promoters such as, e.g., hsp or metallothionein promoter are suitable for eukaryotes expression.

According to the present invention, a total-length Factor VIII-cDNA as well as any of its derivatives comprising Factor VIII:C activity (for instance, B-domain-deleted Factor VIII mutants, Factor VIII mutants including partially deleted B domains) may be used as starting materials for the construction of the modified Factor VIII polypeptide. It may be derived from any mammalian species, preferably human, swine or bovine sources.

The present invention is illustrated in the examples described below. Although illustrative of the present invention in respect to the identification, production and use of enhanced compositions with a reduced binding to LRP of the light chain of Factor VIII, the present invention also should be interpreted to be applicable to the LRP binding of the heavy chain of Factor VIII. Variations known by those of ordinary skill in the art are to be regarded as falling within the scope of the present invention. Unless otherwise defined, all technical and scientific terms used herein have the same meaning as generally understood by the average skilled artisan in the field to which the present invention pertains. Although any methods and materials similar or equivalent to those described herein may be employed in practising or testing the present invention, preferred methods and materials will now be described.

EXAMPLES

Example I

The Light Chain of Factor VIII has an LRP Binding Site

The binding of Factor VIII and subunits of the same to low density lipoprotein receptor-related protein (LRP) was examined using purified components. LRP, Factor VIII, the light chain of Factor VIII, the heavy chain of Factor VIII, and thrombin-activated Factor VIII were obtained using established methods (Moestrup S. K. et al., J. Biol. Chem., Vol. 266, 1991, pp. 14011-14017; Lenting P. J. et a!., J. Biol. Chem., Vol. 269, 1994, pp. 7150-7155; and Curtis J. E. et al., J. Biol. Chem., Vol. 269, 1994, pp. 6246-6250, respectively).

The interaction with LRP was examined on a BIAcore™2000 Biosensor System (Pharmacia Biosensor AB, Uppsala, Sweden) using surface plasmon resonance (SPR) analysis. LRP was immobilized on a CM5 sensor chip at a concentration of 8.3 fmol/mm$^2$, the amine coupling set having been used according to the manufacturer's instructions (Pharmacia Biosensor, Uppsala, Sweden). A control channel on the sensor chip was activated and blocked, using amine coupling reagents without protein immobilization.

Factor VIII or derivatives thereof were passed over the control channel at a concentration of 100 nM in order to assess non-specific binding, and over the LRP-coated channel in 50 mM HEPES (pH 7.4), 150 mM NaCl, 2 mM $CaCl_2$ and 0.005% (v/v) Tween 20 at a flow of 5 ml/min for a period of 2 min at 25° C. The association between the different proteins and LRP is indicated in FIG. 1 and expressed in resonance units. In Table I, the maximum increase in the resonance units for the different derivatives is summarized. The data demonstrated that Factor VIII, thrombin-activated Factor VIII and the light chain of Factor VIII are able to interact with LRP. In contrast, the heavy chain of Factor VIII could not bind LRP. Therefore, it is apparent that the binding moiety of Factor VIII or thrombin-activated Factor VIII for LRP is located in the A3-C1-C2 region (residues 1690-2232).

TABLE I

Binding of Factor VIII and its subunits to immobilized LRP as detected by SPR analysis. Binding to LRP is expressed in resonance units and has been corrected in regard to nonspecific binding.

| Protein | Binding (resonance units) |
|---|---|
| Factor VIII | 262 |
| Heavy chain of Factor VIII | 0 |
| Light chain of Factor VIII | 305 |
| Thrombin-activated Factor VIII | 446 |

Example II

Association Kinetics of Immobilized LRP and the Light Chain of Factor VIII

Figure 2:
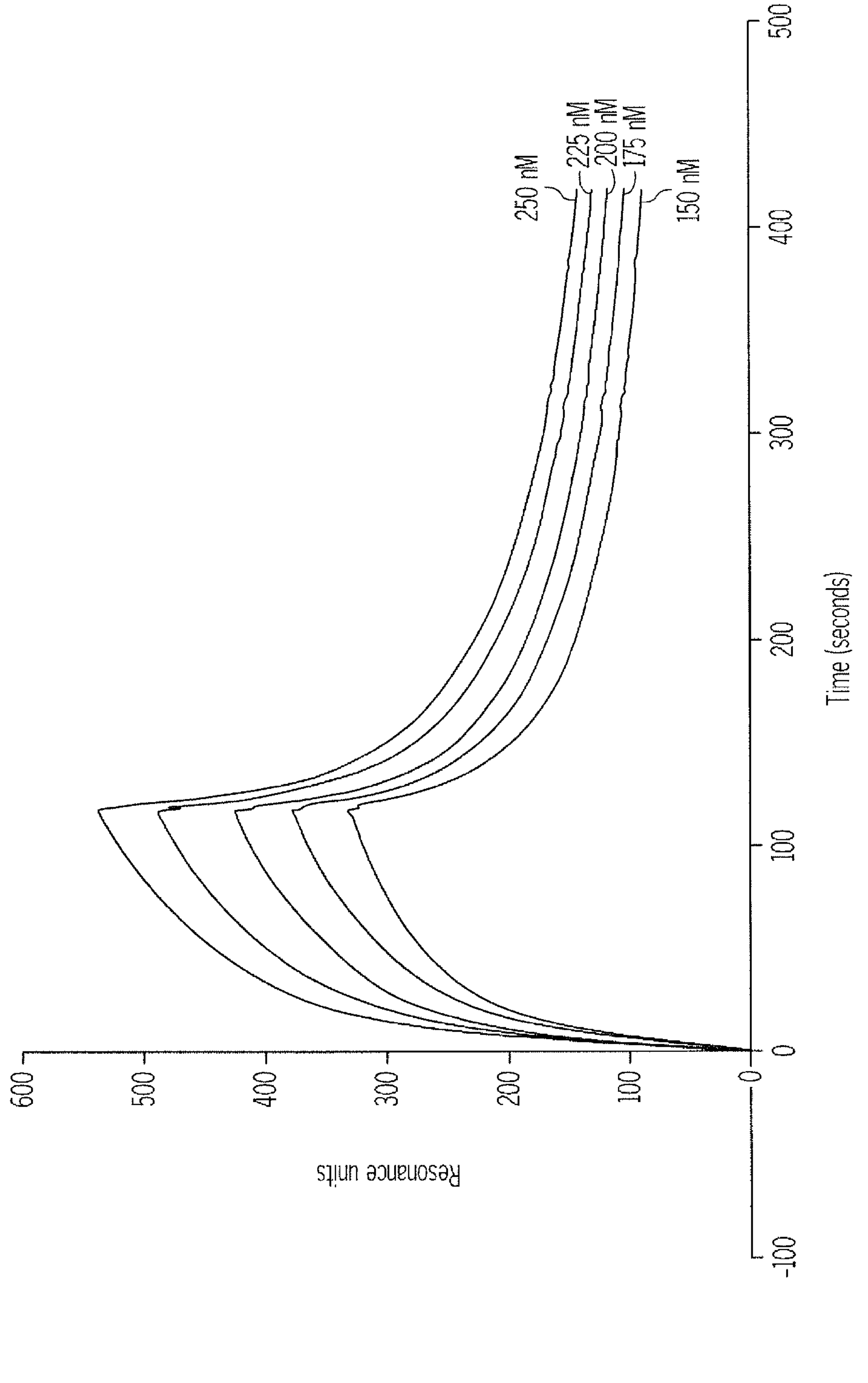
FIG. 2 shows that the light chain of Factor VIII binds to immobilized LRP in a reversible and dose-dependent manner. The kinetic parameters of this interaction are summarized in Table II, which is set forth in Example II. The binding was judged as described in Example II.

The kinetic parameters for the interaction between the light chain of Factor VIII and immobilized LRP were determined on a BIAcore™2000 Biosensor System (Pharmacia Biosensor AB, Uppsala, Sweden) using SPR analysis. This method is generally known in the art and was employed for the kinetic analysis of the interaction between LRP and receptor-associated protein (RAP) (Horn I, in LRP-ligand interactions: kinetics and structural requirements; Ph.D. thesis, 1997, pp. 65-106, Amsterdam University). LRP was immobilized at a concentration of 6.7 fmol/mm$^2$ on three channels of a CM5 sensor chip as described in Example I. A control channel used to evaluate nonspecific binding was prepared as described in Example I. Different concentrations of the light chain of Factor VIII (150, 175, 200, 225 and 250 nM) were passed over the control channel and over the LRP-coated channel in 50 mM HEPES (pH 7.4), 150 mM NaCl, 2 mM CaCl2 and 0.005% (v/v) Tween 20 at a flow of 20 ml/min for a period of 2 min at 25° C. so as to enable association. Subsequently, the channels were incubated with the same buffer at a similar flow so as to enable dissociation. As depicted in FIG. 2, a dose-dependent association and dissociation curve is observed.

The data were analyzed by means of Biacore Evaluation Software (Pharmacia Biosensor AB, Uppsala, Sweden). The data analysis demonstrated that the interaction between the light chain of Factor VIII corresponded best with two classes of binding sites. The association and dissociation rate constants ($k_{on}$ and $k_{off}$, respectively) were calculated for the two binding sites. These speed constants were subsequently used to obtain the equilibrium constants ($K_d$) for these interactions.

TABLE II

Speed constants for the interaction between the light chain of Factor VIII and immobilized LRP. The data analysis indicates the interaction of the light chain of Factor VIII with two classes of bindings sites represented by A and B, respectively.

| Class | kon (M−$^1$s*$^1$) | $ko_{ff}$(s−$^1$) | Kd (=Koff/$ko_n$; nM) |
|---|---|---|---|
| A | 3.0 × $10^5$ | 5.5 × 10'2 | 182 |
| B | 7.2 × $10^4$ | 2.7 × 10''3 | 37 |

Example III

Interaction Between the Light Chain of Factor VIII and Cell-Bound LRP

Since the light chain of Factor VIII binds effectively to LRP in a system in which purified components are used, the interaction between the light chain of Factor VIII and LRP expressed on the surface of living cells was investigated. In order to express the light chain of Factor VIII, i.e., residues 1649 to 2332 (Toole J. J. et al., Nature, Vol. 312, 1984, pp. 342-347), a construct encoding the Factor VIII signal peptide fused to residues 1649 to 2332 was made. This construct was prepared by using the previously described plasmid pBPV-Factor VIII-dB695 (K. Mertens et al., Brit. J. Haematol., Vol. 85, 1993, pp. 133-142) as a template for the preparation of two Factor VIII fragments using polymerase chain reaction (PCR). A fragment was made using the sense primer A1 (5'-TTA GGA TCC ACC ACT ATG CAA ATA GAG CTC TCC-3$^1$) (SEQ ID NO: 1), which contained a BamH1 recognition site and a moiety encoding the N-terminal residues of the Factor VIII signal peptide, and the antisense primer A1 (5'-AGT AGT ACG AGT TAT TTC ACT AAA GCA GAA TCG C-3') (SEQ ID NO: 2) encoding C-terminal residues of the Factor VIII signal peptide and N-terminal residues of the light chain of Factor VIII. A second fragment was made using the sense primer B1 (5'-TTG CGA TTC TGC TTT AGT GAA ATA ACT CGT ACT AC-3$^1$) (SEQ ID NO: 3) encoding the C-terminal residues of the Factor VIII signal peptide and the N-terminal residues of the light chain of Factor VIII, and the antisense primer B1 (5'-ATT GCG GCC GCT CAG TAG AGG TCC TGT GCC TC-3$^1$) (SEQ ID NO: 4) encoding a Not1 recognition site, a stop codon and a moiety encoding the C-terminal residues of the light chain of Factor VIII.

In a second reaction, the products of the two reactions were used as a templates for the construction of the resulting fragment referred to as Factor VIII-SPLC, using primers A1 and B1. Factor VIII-SPLC consisted of a BamH1 recognition site, a moiety encoding the Factor VIII signal peptide and fused to a moiety encoding the light chain of Factor VIII, a stop codon and a Not1 recognition site. Factor VIII-SPLC subsequently was digested with BamH1 and Not1 and ligated into the expression vector pcDNA3, 1 (Invitrogen, Leek, the Netherlands), which was digested using the same restriction enzymes. The resulting vector with the designation pcFactor-VIII-LC was transfected into Chinese hamster ovary K1 (CHO-K1) cells (ATCC CCL-61) using calcium phosphate precipitation (J. Sambrook et al., Molecular Cloning; A Laboratory Manual, Cold Spring Laboratory Press, Cold Spring Harbor, U.S.A., 1989, p. 1637). CHO-K1 cells were established to express LRP. constitutively on its cell surface (D. J. FitzGerald et al., J. Cell. Biol., Vol. 129, 1995, pp. 1533-1541). Stably expressing CHO-K1 cells were obtained at a concentration of 800 μg/ml upon selection with G-148 (Gibco-BRL, Breda, the Netherlands).

Figure 3:
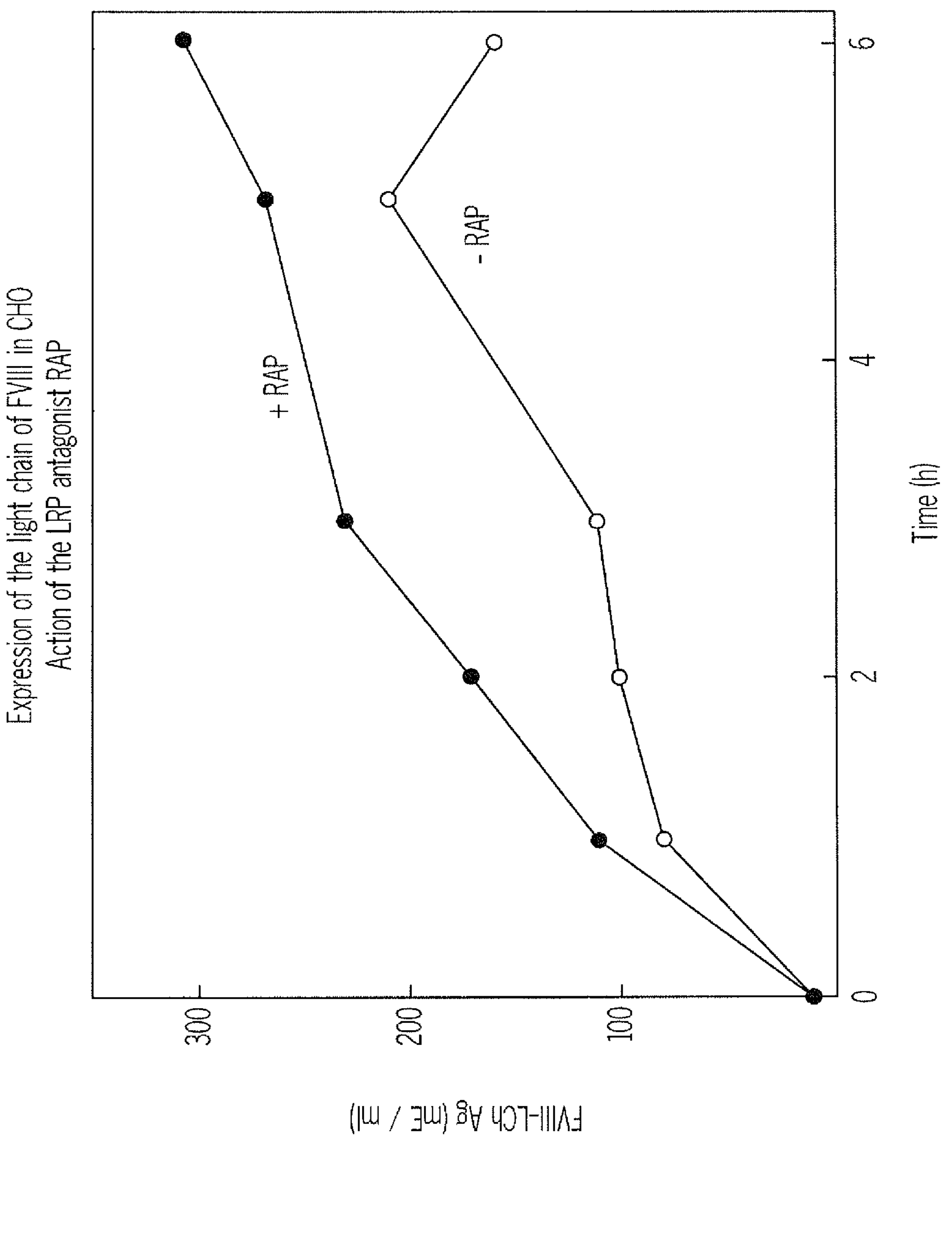
FIG. 3 illustrates the action of the LRP antagonist RAP on the concentration of the light chain of Factor VIII in a medium of cells expressing the light chain of Factor VIII. Assays were carried out as described in Example III. In the absence of RAP (open symbols), the increase in the light chain of Factor VIII within the medium is smaller than in the presence thereof (closed symbols). Data illustrates expression of the light chain of FVIII in CHO cells.

CHO-K1 cells stably expressing the light chain of Factor VIII were grown to confluence in 2 wells of a 6-well plate (Nunc A/S, Roskilde, Denmark). The wells were washed five times using Dulbecco's modified Eagle medium F12 (DMEM-F12) (Gibco, BRL, Breda, the Netherlands) and 1 ml DMEM-F12 was added. In one well, the LRP antagonist, RAP, was added immediately to a concentration of 20 mg/ml at 2 and 4 hours after cell washing. Samples were drawn up to six hours after cell washing and then analyzed for the concentration of the light chain of Factor VIII using a method known in the art (Lenting P. J. et al., J. Biol. Chem., Vol. 269, 1994, pp. 7150-7155). As illustrated in FIG. 3, the concentration of the light chain of Factor VIII in the medium increased with time in the absence of RAP. However, in the presence of RAP, the extent of the increase of the light chain of Factor VIII rose as compared to the absence of RAP. Thus, the inhibition of LRP is associated with an accumulation of the light chain of Factor VIII in the medium. This clearly demonstrates that an LRP-dependent mechanism is involved in the cellular uptake of the light chain of Factor VIII.

Example IV

Figure 4:
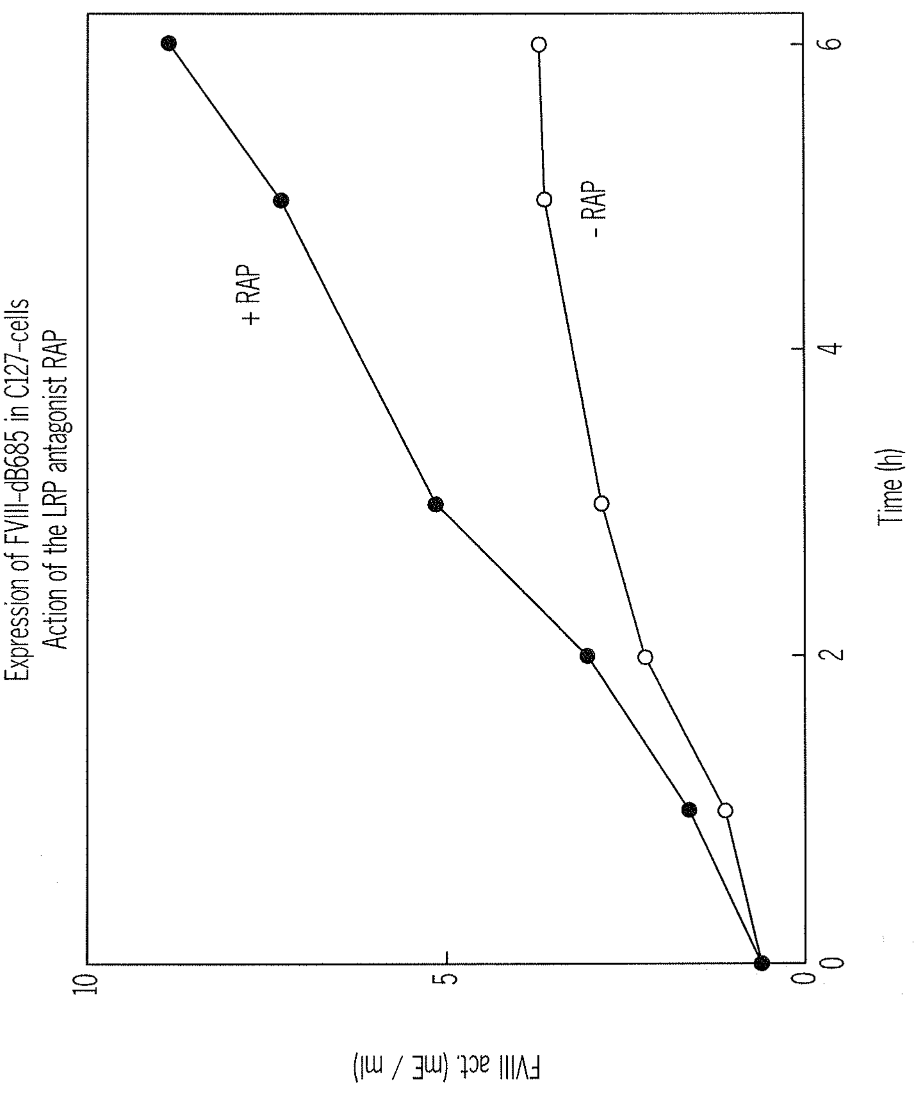
FIG. 4 illustrates the action of the LRP antagonist RAP on the concentration of the intact Factor VIII heterodimer in the medium of the Factor-VIII-expressing cells. The details of the assay are described in Example IV. In the absence of RAP (open symbols), the increase in the Factor VIII activity is smaller than in the presence thereof (closed symbols). Data illustrates expression of FVIII-dB685 in C127-cells.

Interaction, Between Factor VIII and Cell-Surface-Exposed Low Density Lipoprotein Receptor-Related Protein As described in Example III, an interaction occurs between the light chain of Factor VIII and the cell-surface-exposed LRP. Therefore, also examined was whether the intact Factor VIII protein interacts with cell-surface-exposed LRP. A previously established, mouse fibroblast cell line which was stably transfected in order to produce Factor VIII (Mertens K. et al., Brit. J. Haematol., Vol. 85, 1993, 133-142) was grown to confluence in 2 wells of a 6-well plate (Nunc A/S, Roskilde, Denmark). The cells were washed five times using Iscov's modified Eagle medium (IMEM) (Boehringer Ingelheim/Biowhitaker, Verviers, Belgium), and 1 ml IMEM was added. In one well, LRP antagonist, RAP, was added immediately, to a concentration of 20 mg/ml at 2 and 4 hours after cell washing. Samples were drawn up to six hours after cell washing and then analyzed for Factor VIII-cofactor activity using an already established method (Mertens K. et al., Brit. J. Haematol., Vol. 85, 1993, 133-142). As shown in FIG. 4, the amount of Factor VIII-cofactor activity in the medium increases with time in the absence of RAP. However, in the presence of RAP, the extent of the increase of Factor VIII rose as compared to the absence of RAP. Thus, the inhibition of LRP is associated with an accumulation of Factor VIII in the medium. Therefore, it is apparent that an LRP-dependent mechanism is involved in the cellular uptake of the light chain of Factor VIII.

Example V

The Action of RAP on the Factor VIII Pharmacokinetics in Knock-Out Mice Suffering from Severe Factor VIII Deficiency A mouse strain suffering from severe Factor VIII (FVIII) deficiency was recombinantly created by the selective disruption of the mouse Factor VIII gene according to Bi et al., Nature Genetics, 1995, Vol. 10, pp. 119-121. Factor VIII knock-out mice were created by inserting a neo-gene into the $3^1$ end of exon 17 of the mouse Factor VIII gene. The affected male animals (X"Y) had nondetectable Factor VIII levels of <0.02±0.01 U/ml when measurements were carried out either by a chromogenic Factor VIII test, Hyland Immuno, Vienna, Austria, as recently described (Turecek et al., Thromb. Haemostas. Suppl., 1997, Vol. 769) or by antigen ELISA as described below.

Two affected hemizygous male mice (X'Y) were intravenously treated with a dose of 200 U/kg body weight of a recombinant human Factor VIII (rhFVIII) preparation which was derived from Chinese hamster ovary cells produced as described (WO/85/01961) and pharmaceutically formulated without stabilizing protein.

One hour after treatment, the tips of the tails of the narcotized mice were incised by the edge of a scalpel as described by Novak et al., Brit. J. Haematol. Vol. 69, 1998, pp. 371-378. A volume of 50 μl blood was collected from the tail wounds by means of capillary tubes (Ringcaps, Hirschmann, Germany), which capillary tube were coated with lithium heparin as an anticoagulants. The capillary tubes were closed and centrifuged to separate blood cells and plasma. The capillary tubes were opened, and the cell and plasma fractions were collected by further centrifugation. Finally, the plasma samples were subjected to Factor VIII determination by means of Factor VIM antigen ELISA, test set IMMUNOZYM FV111 Ag, Hyland Immuno, Vienna, Austria, using monoclonal anti-Factor-VIII-antibodies both for capturing and for detection as described in Stel et al., Nature, 1983, Vol. 303, pp. 530-532; Lenting et al., J. Biol. Chem., Vol. 269, 1994, pp. 7150-7155; Leyte et al., Biochem. J., Vol. 263, 1989, pp. 187-194. The resulting Factor VIII values were expressed in International Units of human Factor VIII. The results of the Factor VIII plasma levels are indicated in the Table.

Two other affected hemizygous male mice (X'Y) were pretreated with recombinant receptor-associated protein (GST-RAP) 10 minutes prior to the treatment with recombinant human Factor VIII at a dose of 40 mg/kg body weight. The RAP used in this assay, which interacts with LRP, was obtained by bacterial fermentation as described by Hertz et al. (J. Biol. Chem., Vol. 266, 1991, pp. 21232-21238). A fusion protein of RAP with glutathion-S transferase was expressed in *E. coli* and purified by affinity chromatography on glutathione agarose. The resulting protein primarily consisted of the fusion protein and cleavage products of RAP and glutathione-S transferase. The fusion protein was formulated in an injectable buffer ready for administration to the Factor VIII knock-out mice. As in the control group (treatment solely with Factor VIII), blood samples were drawn one hour after the administration of recombinant Factor VIII and measured for their Factor VIII activity using Factor VIII antigen ELISA. The results are indicated in Table III.

TABLE III

| Mouse no. | Treatment Dose GST-RAP | Treatment Dose RhFVIII | Recovery 1 h after treatment FVIII:Ag (U/ml plasma) |
|---|---|---|---|
| 1 | 40 mg/kg | 200 U/kg | 1.92 |
| 2 | 40 mg/kg | 200 U/kg | 1.88 |
| 3 | — | 200 U/kg | 0.73 |
| 4 | — | 200 U/kg | 0.83 |

In mice pretreated with GST-RAP, the Factor VIII level was more than 200% of the plasma levels after treatment with recombinant Factor VIII alone. The administration of the LRP antagonist, RAP, enhanced the pharmacokinetics of Factor VIII.

Example VI

Figure 5A:
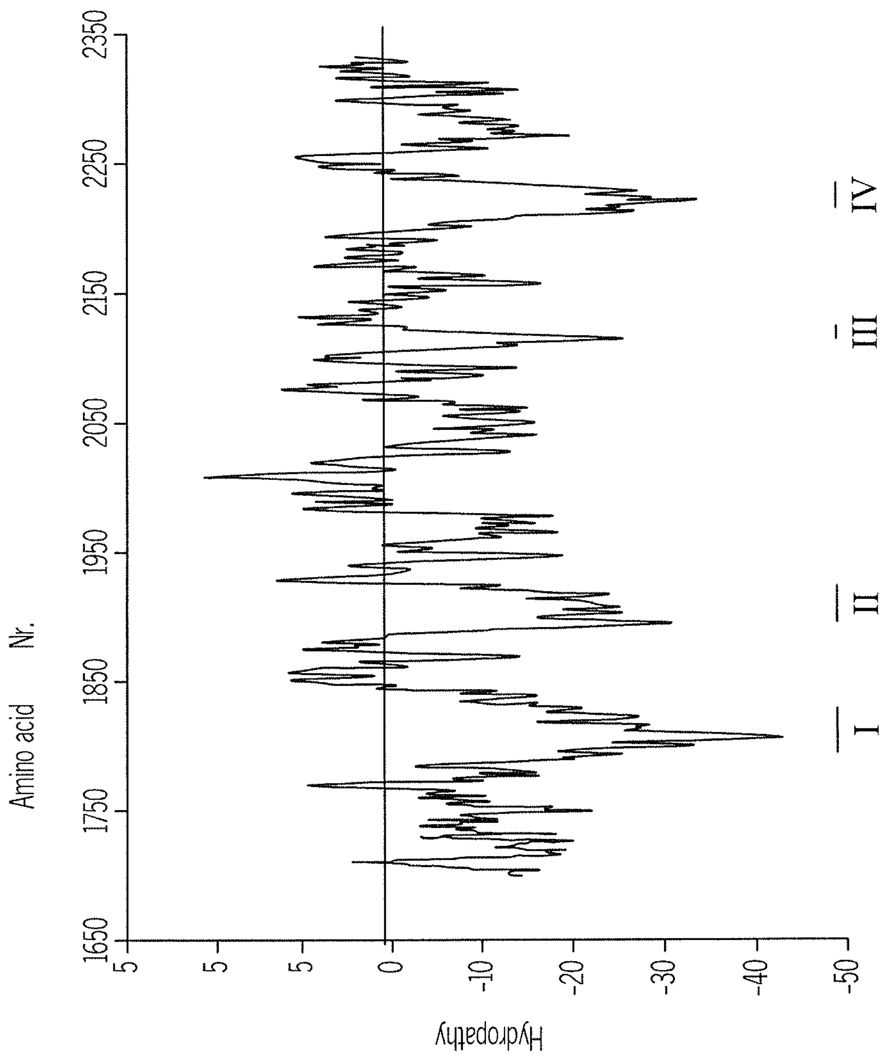
FIGS. 5A and 5B illustrate hydropathy plots of the domains A3, C1 and C2 of the light chain of Factor VIII. The plot was established as described in Example VI. The plot shows the presence of different individual regions of low hydropathy values indicating the hydrophilic nature of potentially exposed exosites. They are shown as A to K (FIG. 5A) and I to IV (FIG. 5B).
Figure 5B:
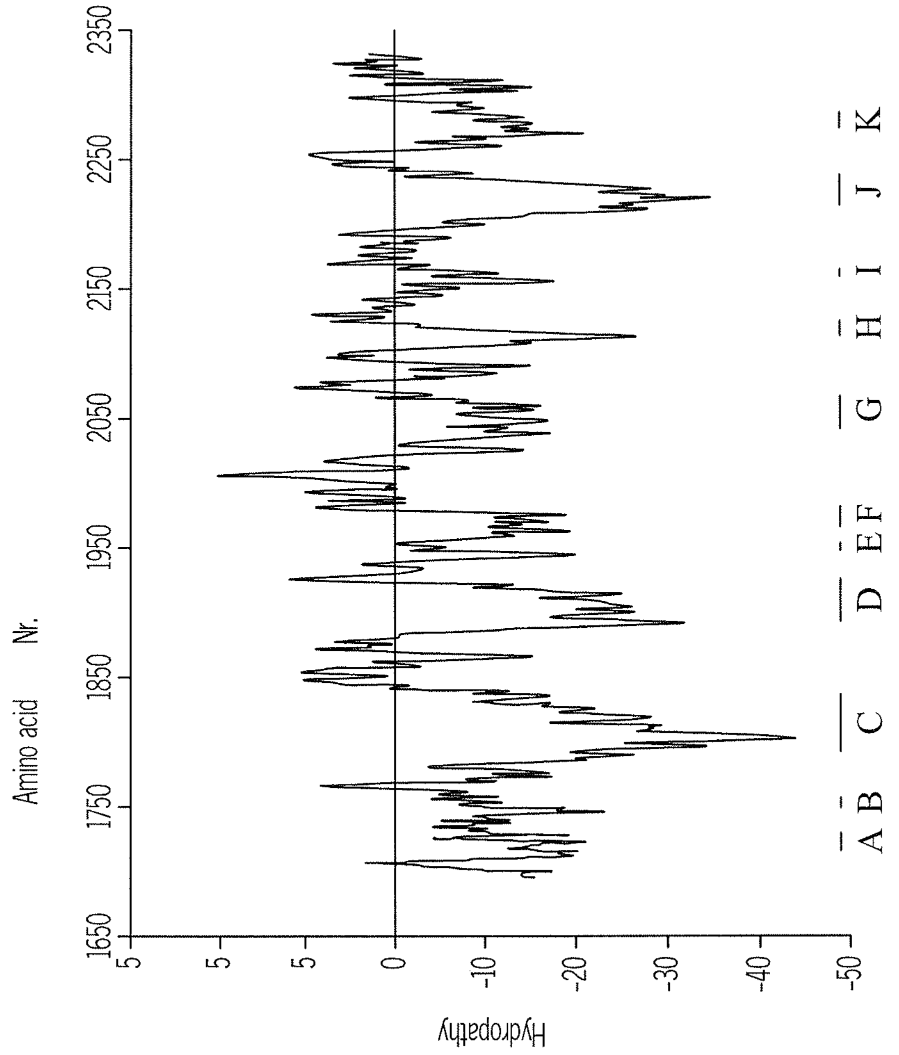

Identification of Potential LRP Binding Exosites on the Light Chain of Factor VIII A method for identifying exosites that may be involved in protein interaction, has already been established (J. Kyte and R. F. Doolittle, J. Mol. Biol. Vol. 157, 1982, pp. 105-132). The method provides a program continuously evaluating the hydrophilicity and hydrophobicity of a protein along its amino acid sequence. The method employs a hydropathy scale that indicates the average hydropathy within segments of predetermined sizes along the amino acid sequence. Hydrophilic sections are characterized by negative hydropathy values, and these sections are probably oriented to the external side of a protein present in an aqueous solution. This method was applied to the known sequence of human Factor VIM (G. A. Vehar et al., Nature, Vol. 312, 1984, pp. 337-342; J. J. Toole et al., Nature, Vol. 312, 1984, 342-347) using a segment size ("window") of 19 residues. From the complete sequence of Factor VIII, the region 1690-2332 corresponding to the Factor VIII A3/C1/C2 domain was subjected to this analysis, and the resulting hydropathy plot, having a cut-off value of −15, is illustrated in FIGS. 5A and 5B.

The results of this method show several isolated regions having low hydropathy values, which reflect the hydrophilic nature associated with potential exosites. The potential exosites are denoted by A to K (Table IV):

TABLE IV

| Site | Residues | Domain |
|---|---|---|
| A | Met 1711 to Gly 1725 | A3 |
| B | Phe1743toArg1749 | A3 |
| C | Ser 1784 to Asp 1831 | A3 |
| D | Ser 1888 to His 1919 | A3 |
| E | Trp 1942 to Met 1947 | A3 |
| F | Ser 1959 to Ala 1974 | A3 |
| G | Ile 2037 to Trp 2062 | C1 |
| H | Asp 2108 to Asn 2118 | C1 |
| I | Thr 2154 to Ile 2158 | C1 |
| J | Arg 2209 to Phe 2234 | C2 |
| K | His 2269 to Lys 2281 | C2 |

TABLE V

| Site | Residues | Domain |
|---|---|---|
| I | Phe 1785 to His 1822 | A3 |
| II | Trp 1889 to Asn 1915 | A3 |
| III | Trp 2112 to Tyr 2115 | C1 |
| IV | His 2211 to Leu 2230 | C2 |

From the complete sequence of Factor VIII, the region 1690-2332 corresponding to the light chain of complete Factor VIII, was subjected to this analysis, and the resulting hydropathy plot, which has a cut-off value of −20, is illustrated in FIG. 5B. The exosites are denoted by I to IV.

Example VII

The C2 Domain of Factor VIII Includes an LRP Binding Site

The A3-C1-C2 region of Factor VIII comprises the binding moiety for LRP (cf. Example I). This region contains a number of potential LRP binding exosites in the domains constituting them, including the C2 domain (cf. Example VI). To demonstrate that such exosites might actually be involved in LRP binding, the interaction between LRP and the C2 domain of Factor VIII was analyzed more thoroughly. The C2 domain of Factor VIII (i.e., residues 2171-2332) was expressed in insect cells using an established method (K. Fijnvandraat et al., Blood, Vol. 91, 1998, pp. 2347-2352). The C2 domain of Factor VIII was purified by immunoaffinity chromatography using the monoclonal antibody CLB-CAg 117 directed to the C2 domain (K. Fijnvandraat et al., Blood, Vol. 91, 1998, pp. 2347-2352). The interaction with LRP was assayed on a BIAcore™2000 System (Pharmacia Biosensor AB, Uppsala, Sweden) using surface plasmon resonance (SPR) analysis. LRP was immobilized on a CM5 sensor chip as described in Example I. In order to enhance the resonance signal, the C2 domain of Factor VIII (0, 100 or 275 nM) was preincubated in the presence of 500 nM of the monoclonal antibody ESH-8 directed at the C2 domain (D. Scandella et al., Blood, Vol. 86, 1995, pp. 1811-1819), in 50 mM HEPES (pH 7.4), 150 mM NaCl, 2 mM $CaCl_2$, 0.005% (v/v) Tween 20 for 15 min at room temperature. The preincubated samples were then passed over the control channel in order to assess nonspecific binding, as well as over the LRP-coated channel (8.3 fmol/$mm^2$), at a flow of 5 ml/min for 2 min at 25° C.

Figure 6:
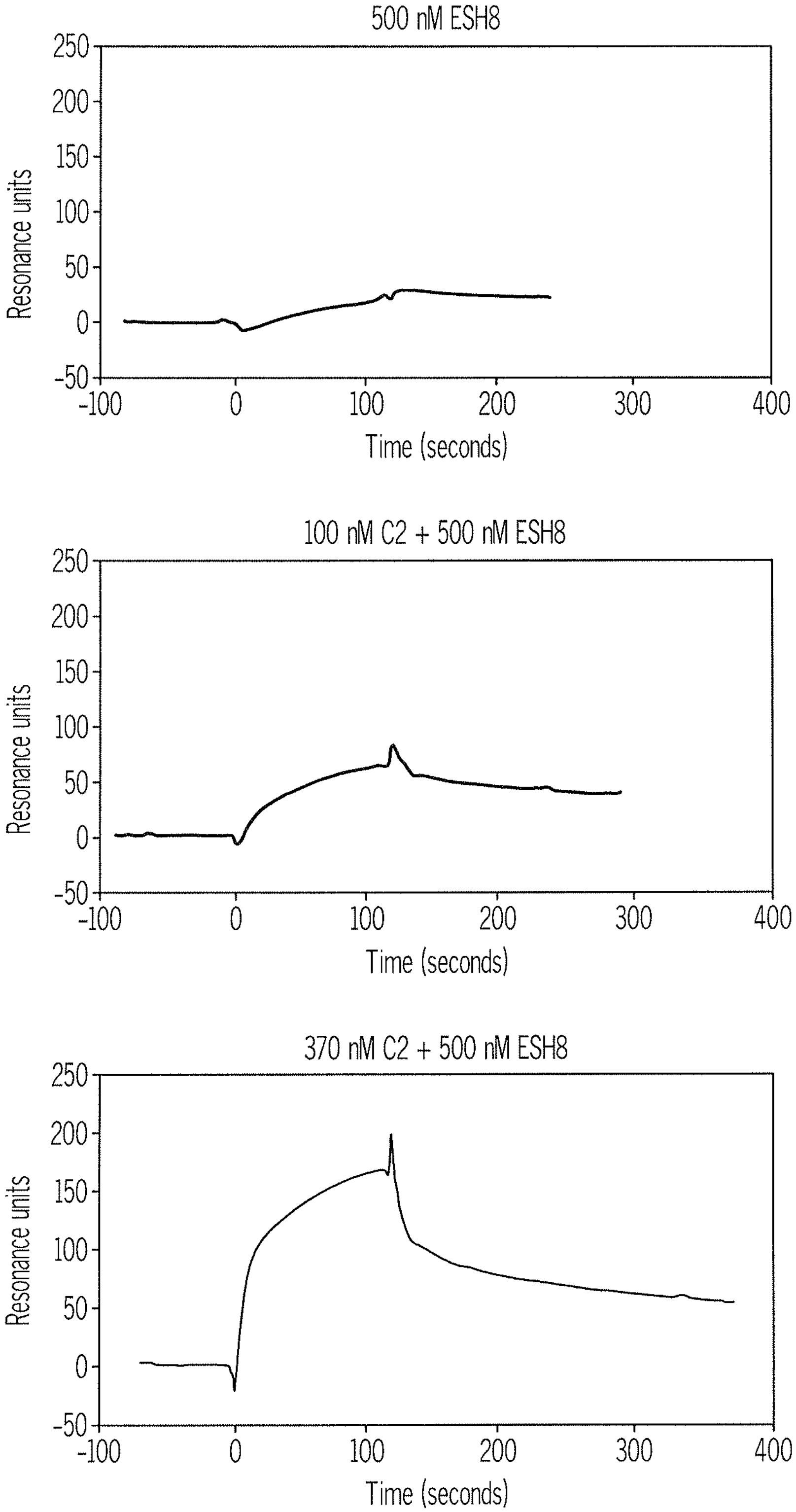
FIG. 6 illustrates the interaction of the C2 domain of Factor VIII with immobilized LRP in the presence of the C2-domain-directed antibody ESH-8. Binding was analyzed using surface plasmon resonance as described in Example VII. In the absence of the C2 domain, ESH-8 does not show any significant binding to immobilized LRP. In the presence of the C2 domain, a dose-dependent increase in the binding to LRP is, however, observed. This demonstrates that the C2 domain of Factor VIII binds to LRP.

In the absence of the C2 domain, ESH-8—if at all—shows a minimum binding to immobilized LRP. However, in the presence of the C2 domain, a dose-dependent increase in the binding to LRP was observed (FIG. 6). This demonstrates that the C2 domain of Factor VIII binds to LRP. Thus, the exosites within the light chain of Factor VIII are definitely capable of LRP binding and are involved in the LRP-dependent clearance of Factor VIII in vivo.

It will be readily understood by the skilled artisan that the present invention is well apt to fulfill the tasks and achieve the mentioned as well as inherent goals and advantages. The compounds, methods, and compositions described herein are illustrated as representative of the preferred embodiments. They are intended to exemplify the invention without restricting its scope. Modifications and other uses are readily conceivable by the skilled artisan and are intended to be encompassed by the spirit of the invention and the scope of the annexed claims.

Example VIII

Binding of the Factor VIII C2 Domain in the Presence of an Anti-Factor VIII-C2-Domain-Antibody The Factor VIII (FVIII) molecule comprises two sites which are involved in vWF binding, one of these sites being located on the carboxy-terminal C2 domain of the light chain of Factor VIII (Saenko and Scandella, J. B. C. 272 (1997), pp. 18007-18014). Since vWF binding is inhibited by the antibody ESH4 directed against the C2 domain, this effect was examined for LRP binding. The antibody binding body examinations having been carried out as described in Example VII. The antibody ESH4 was obtained from American Diagnostica.

Figure 7:
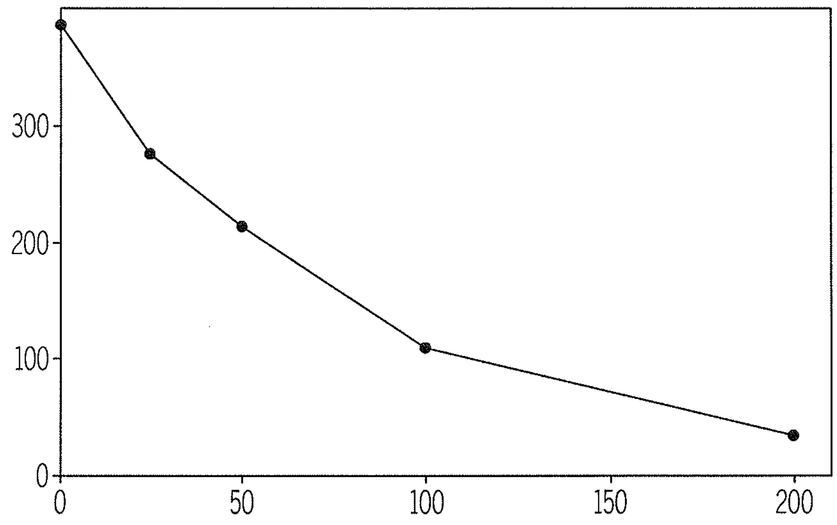
FIG. 7 illustrates the binding of the C2 domain of Factor VIII to LRP in the presence of ESH4.

As illustrated in FIG. 7, ESH4 interferes with the binding of LRP to the light chain of Factor VIII. This inhibition appears to be specific, since ESH4 was not able to influence the binding of tissue-type plasminogen activator/plasminogen activator inhibitor 1 complexes to LRP. Moreover, other antibodies which were directed against the light chain of Factor VIII, i.e., CLB-CAg A and CLB-CAg 69 (Lenting et al., J. B. C. 269 (1994), pp. 7150-7155) were not able to interfere with LRP as regards the binding to Factor VIII.

FIG. 7 depicts the binding of the Factor VIII C2 domain to LRP in the presence of ESH4. To this end, immobilized LRP (16 fmol/$mm^2$) was incubated with the light chain of Factor VIII (150 nM) in the presence or absence of antibody ESH4 at a flow of 5 μl/min for 2 min at 25° C. The results were indicated in resonance units (RU) and corrected against nonspecific binding, which was less than 5% as compared to the binding to LRP-coated channels.

In FIG. 7, the concentration of ESH4 antibody in nM was plotted on the X-axis and the remaining binding of the light chain of Factor VIII in RU was plotted on the Y-axis.

Example IX

The Factor VIII A3-C1 Region Comprises an LRP Binding Site

The A3-C1-C2 region of Factor VIII comprises the binding moiety for LRP (cf. Example (I). From the kinetic analysis described in Example II, it is clearly apparent that multiple sites involved in LRP are present (Table II, class A and class B binding sites). As indicated in Example VII, the presence of such interactive sites for the region of the Factor VIII C2 domain was confirmed (cf. also FIG. 6). In order to confirm that also other exosites are involved in the interaction with LRP, the interaction between LRP and the Factor VIII A3-C1 region (i.e., Factor VIM residues 1649 to 2172) was analyzed. In order to obtain the fragment of the light chain of this Factor VIII, a construct encoding the Factor VIII signal peptide fused to residues 1649 to 2172 was prepared. This construct was prepared by the following method. The vector pcFactor VIII-LC described in Example III was used as a conformation template for the construction of a Factor VIII fragment using PCR. This fragment was produced using the sense primer A1 (5'-TTA GGA TCC ACC ACT ATG CAA ATA GAG CTC TCC-3') (SEQ ID NO: 1) and the antisense primer FA2172min (5'-AAT GCG GCC GCT TCA ATT TAA ATC ACA GCC CAT-3[1]) (SEQ ID NO: 5). The primer FA 2172 encodes a Not1 recognition site, a stop codon and the residues 2167 to 2172 of Factor VIII. The PCR product was cleaved with BspMII and NotI, and a 352 base pair fragment was isolated and ligated into the pcFactor VIII-LC vector, which was digested using the same restriction enzymes. The resulting vector, which was designated as pcFactor VIII-A3C1, was transfected on CHO-K1 cells (ATCC CCL-61) using calcium phosphate precipitation (J. Sambrook et al., Molecular Cloning; A Laboratory Manual, Cold Spring Laboratory Press, Cold Spring Harbor, U.S.A., 1989, p. 1637). CHO-K1 cells which stably express Factor VIII A3-C1 cells were obtained at a concentration of 800 ug/ml upon selection with G-148 (Gibco-BRL, Breda, the Netherlands).

CHO-K1 cells stably expressing Factor VIII A3-C1 fragments were used for large-scale cultivation in order to obtain a conditioned medium containing Factor VIII A3-Cl. Factor VIII A3-C1 was purified by immunoaffinity chromatography using the previously described monoclonal antibody CLB-CAg A (Leyte A. et al., Biochem. J., 1989, Vol. 263, pp. 187-194) directed against the A3 domain of Factor VIII. To this end, CLB-CAg A was immobilized on CNBr Sepharose 4 B (Pharmacia Biotech, Roosendaal, the Netherlands) according to the manufacturer's instructions at a concentration of 1 mg/ml. A Conditioned medium was incubated with CLB-CAg A Sepharose (2 ml per liter medium) and bound Factor VIIIA3-C1 was eluted in 150 mM NaCl, 55% (v/v) ethyleneglycol, 25 mM lysine (pH 11). Factor VIII A3-C1 containing fractions were immediately neutralized using 1/10 volume of 1 M imidazole (pH 5.0) and then dialyzed against 150 mM NaCl, 2 mM $CaCl_2$ and 0.005% (v/v) Tween 20, 20 mM HEPES (pH 7.4).

The interaction between Factor VIII A3-C1 and LRP was investigated on a BIAcore™2000 Biosensor System (Pharmacia Biosensor AB, Uppsala, Sweden) using surface plasmon resonance analysis. LRP was immobilized on a CM5 sensor chip as described in Example I. Samples that contained Factor VIII A3-C1 (200 nM or 400 nM) were passed over the control channel at a flow of 5 μl/min for a period of 2 min at 25° C. to assess nonspecific binding and over the LRP-coated channel (8.3 fmol/$mm^2$). In Table VI, the maximum increase in the resonance units for both concentrations of Factor VIII A3-C1 is summarized. In the presence of 400 nM Factor VIII A3-C1 a higher response was observed than with 200 nM Factor VIIIA3-C1 (59 and 47 resonance units, respectively). In order to enhance the binding of Factor VIII A3-C1 to LRP, Factor VIII A3-C1 (400 nM) was preincubated in the presence of 500 nM of the monoclonal antibody CLB-CAg A in 50 mM HEPES (pH 7.4), 150 mM NaCl, 2 mM $CaCl_2$, 0.005% (v/v) TWEEN 20 for 15 min at room temperature. The preincubated samples were then passed over the control channel and over the LRP-coated channel at a flow of 5 ml/min for 2 min at 25° C.

In the presence of antibody CLB-CAg A, a rise in the response was actually observed (118 resonance units). Thus, the data clearly demonstrate that Factor VIII A3-C1 is able to interact with LRP in a dose-dependent manner.

TABLE VI

Binding of Factor VIIIA3-C1 to immobilized LRP as detected using SPR analysis. Binding to LRP is expressed in resonance units and has been corrected for nonspecific binding.

| Concentration A3-C1 | Binding (resonance units) |
|---|---|
| 200 nM | 47 |
| 400 nM | 59 |
| 400 nM + 500 nM CLB-CAg A | 118 |

Example X

Figure 8:
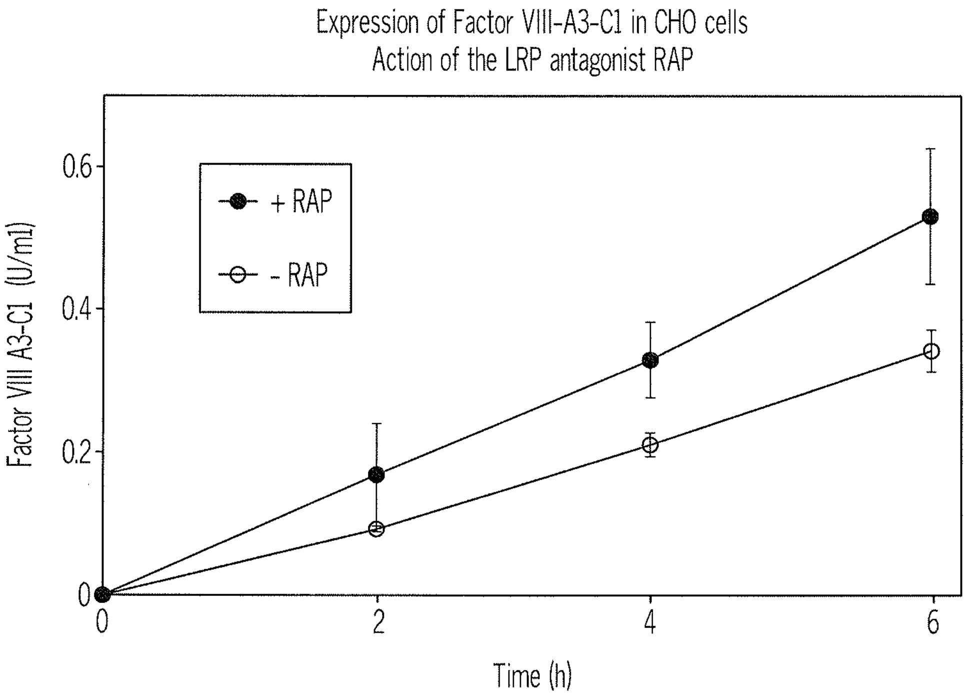
FIG. 8 illustrates the effect of RAP on the expression of Factor VIII-A3-C1 in CHO-K1 cells.

Interaction Between Factor VIII A3-C1 and Cell-Surface-Exposed Low Density Lipoprotein Receptor-Related Protein As described above, Factor VIII A3-C1 (i.e., residues 1649 to 2172) is able to interact with purified LRP. Furthermore, the interaction between Factor VIIIA3-C1 and LRPexpressed on the surface of living cells was investigated. CHO-K1 cells stably expressing Factor VIII A3-C1 (as described above) were, therefore, grown to confluence in 6 different wells of a 24-well plate (Nunc A/S, Roskilde, Denmark). The wells were washed five times using DMEM-F12 (Gibco-BRL, Breda, the Netherlands) and 500 μl DMEM-F12 were added. In three of the wells, the LRP-antagonist RAP was added at a concentration of 1 μM at 2 and 4 hours after cell washing. Samples were drawn up to 6 hours after cell washing and then analyzed for their Factor VIII A3-C1 concentrations. The concentrations of Factor VIII A3-C1 were determined substantially using a method described in the art. (Lenting P. J. et al., J. Biol. Chem., Vol. 269, 1994, pp. 7150-7155), except that the monoclonal antibody CLB-CAg 12 was used instead of CLB-CAg 117. As illustrated in FIG. 8, the concentration of Factor VIII A3-C1 increased with time in the absence of RAP. However, in the presence of RAP, the extent of Factor VIII A3-C1 rises as compared to the absence of RAP. Thus, the inhibition of RAP is associated with an accumulation of Factor VIII A3-C1 in the medium. This demonstrates that an LRP-dependent mechanism is involved in the cellular uptake of Factor VI11 A3-C1.

FIG. 8 shows the effect of the LRP antagonist RAP on the concentration of Factor VIII A3-C1 in a medium of Factor-VIII-A3-C1-expressing cells. In the absence of RAP (open symbols), the rise in Factor VIII A3-C1 levels is lower than in the presence of RAP (closed symbols). The data represent the mean values±standard deviation of the three assays.

Example XI

Mutations in the Factor VIII C2 Domain Affect Binding to LRP

As described in Example VII, the Factor VIII C2 domain comprises a binding site for LRP. Therefore, the effects of mutations in this domain on the binding of Factor VIII and the interaction with cell-surface-exposed LRP were studied. In order to express Factor VIII variants comprising such mutations, two constructs were prepared. Both Factor VIII expression plasmids were derivatives of the plasmid pF8-SQ#428 (F. Scheiflinger, unpublished results); a plasmid containing the cDNA of a B-domain-deleted FVIII variant inserted in the commercially available vector pSI (Promega). In this construct, all but fourteen amino acids of the B domain of FVIII were removed <SQ mutant, cf. Lind et al., Eur. J. Biochem., Vol. 232, 1995, p. 19-27).

Vector pF8-SQ#428 was modified by cutting with EcoRV/AgeI and ligating the annealed oligonucleotides P-A/Em(1) 5'-CCGGAGATTA TTACGAGGAC AGTTATGAAG AC-3' (SEQ ID NO: 6) and P-A/Em(2) 5'-GTCTTCATAA CTGTC-CTCGT AATAATCT-3' (SEQ ID NO: 7). This procedure resulted in vector pF8-SQ-dA/E#501. Within this vector, the expression of FVIII-cDNA is driven by the SV40 promoter and enhancer. Downstream, at the 3' end of the FVIII gene, the polyadenylation site of SV40 is used to terminate the transcription. A chimeric intron composed of the 5'-donor site from the first intron of the human β-globin gene and the branch and 3'-acceptor site from the intron located between the leader and the body of a variable region of a heavy chain of an immunoglobulin gene was introduced to increase the level of gene expression (cf. pSI, product information, Promega). In order to further improve expression levels, a sequence context found to be optimal for the initiation of eukaryotic protein translation ("Kozak sequence" 5'-GC-CACCATG-3') was inserted immediately upstream of the Factor VIII start codon (Kozak, J. Biol. Chem., Vol. 266, 1991, pp. 19867-19870). The vector pF8-SQ-dA/E#501 was then used to construct vectors pC2-m7#516 and pC2-m9#518.

The construction of pC2-m7#516 was effected by the insertion of annealed oligonucleotides Mu(1) 5'-CGAAT-TCACC CCCAGATTTG GGAACACCAG ATTGCCCTGA GGCTGGAGAT TCTGGGCTGC GAGGCACAGC AGCAGTACTG AGC-3[1] (SEQ ID NO: 8) and P-Mu(2) 5'-GGCCGCTCAG TACTGCTGCT GTGCCTCGCA GCCCAGAATC TCCAGCCTCA GGGCAATCTG GTGT-TCCCAA ATCTGGGGGT GAATT-3' {SEQ ID NO: 9) into AsuII/NotI-cut vector pF8-SQ-dA/E#501.

The resulting vector encodes a Factor VIII variant comprising the following substitutions: $Ser^{2312}$ to $Ile^{2312}$, $Val^{2314}$ to $Glu^{2314}$, $Met^{2321}$ to $Leu^{2321}$, $Val^{2323}$ to $He^{2323}$, $Asp^{2330}$ to $Gln^{2330}$ and $Leu^{2331}$ to $Gln^{2331}$.

The construction of pC2-m9#518 was effected by the insertion of annealed oligonucleotides P-CC(1) 5'-CTA-GAACCAC CGTTAGTGGC TCGCTACGTG CGACTG-CACC CCCAGAGTTG GGCTCACCAT-3', P-CC(2) (SEQ ID NO: 10); 5'-ATTGCCCTGA GGCTGGAGGT TCTGGGCTGC GATACTCAGC AGCCAGCTTG AGC-3', P-CC(3)(SEQIDNO:11).

5'-GGCCGCTCAA GCTGGCTGCT GAGTATCGCA GC-3', P-CC(4) (SEQ ID NO: 12) 5'-CCAGAACCTC CAGCCTCAGG GCAATATGGT GAGCCCAACT CTGGGGGTGC-3' and P-CC(5) (SEQ ID NO: 13).

5'-AGTCGCACGT AGCGAGCCAC TAACGGTGGT T-3' (SEQ ID NO: 14) into XbaI/NotI-cut vector pF8-SQ-dA/E#501.

The construct pC2-m9#518 encodes a Factor VIII variant comprising the following amino acid substitutions: $Asp^{2298}$ to $Glu^{2298}$, $Leu^{2302}$ to $Val^{2302}$, $Thr^{2303}$ to $Ala^{2303}$ and $Leu^{2306}$ to $Val^{2306}$, $Ile^{2308}$ to $Leu^{2308}$, $Val^{2314}$ to $Ala^{2314}$, $Gln^{2316}$ to $His^{2316}$, $Mel^{2321}$ to $Leu^{2321}$, $Glu^{2327}$ to $Asp^{2327}$, $Ale^{2328}$ to $Thr^{2328}$, $Asp^{2300}$ to $Gln^{2330}$, $Leu^{2331}$ to $Pro^{2331}$ and $Tyr^{2332}$ to $Ala^{2332}$.

Both vectors pC2-m9#518 and pC2-m7#516 respectively encoding Factor VIII#518 and Factor VIII#516 were transfected into mouse fibroblast C127 cells using calcium phosphate precipitation (J. Sambrook et al., Molecular Cloning; A Laboratory Manual, Cold Spring Laboratory Press, Cold Spring Harbor, U.S.A., 1989, p. 1637). The vectors were cotransfected (20:1 ratio) using the plasmid pDH#310, thus allowing a selection of the transfectants with hygromycin B (200 μg/ml).

C127 cells stably expressing normal Factor VIM (cf. Example IV), Factor VIII#518 and Factor VIII#516 were grown to 50% confluence in 4 wells of a 24-well plate (Nunc A/S, Roskilde, Denmark). The wells were washed five times using IMEM (Boehringer Ingelheim/BioWhitaker, Verviers, Belgium) and 1 ml IMEM was added. In two of the wells for each Factor VIII variant, the LRP-antagonist RAP was added immediately to a concentration of 20 mg/ml and 2 hours after cell washing. Samples were drawn two and three hours after cell washing and then analyzed for Factor VIII cofactor activity using an established method (Mertens K. et al., Brit. J. Haematol., Vol. 85, 1993, 133-142). In Table VII, the Factor VIII expression levels in the presence and absence of RAP at different points of time are indicated. For normal Factor VIII as well as Factor VIII variants #516 and #518, an increase in the Factor VIII activity in the medium is observed in the presence or absence of RAP. For normal Factor VIII the expression level is, however, elevated in the presence of RAP, whereas for Factor VIII variants #516 and #518 this effect is strongly reduced, if present at all. This demonstrates that the LRP-mediated cellular uptake of Factor VIM variants #516 and #518 proceeds less efficiently than with normal Factor VIII. Thus, amino acid substitutions in the Factor VIII C2 domain as indicated for Factor VIII variants #516 and #518 render Factor VIII less sensitive to LRP-mediated cellular uptake.

TABLE VII

Expression levels of normal Factor VIII and Factor VIII variants #516 and #518 in the presence and absence of RAP. The data represent the ± mean values of two independent assays.

| | | Expression (U/L) | | Ratio |
|---|---|---|---|---|
| Factor VIII | Time (h) | −RAP | +RAP | +RAP/−RAP |
| Normal | 2 | 1.3 ± 0.1 | 4.2 ± 0.4 | 3.2 |
| | 3 | 2.2 ± 0.2 | 5.0 ± 0.3 | 2.3 |
| #516 | 2 | 0.3 ± 0.2 | 0.3 ± 0.2 | 1.0 |
| | 3 | 0.6 ± 0.1 | 0.8 ± 0.3 | 1.3 |

TABLE VII-continued

Expression levels of normal Factor VIII and Factor VIII variants #516 and #518 in the presence and absence of RAP. The data represent the ± mean values of two independent assays.

| | | Expression (U/L) | | Ratio |
|---|---|---|---|---|
| Factor VIII | Time (h) | −RAP | +RAP | +RAP/−RAP |
| #518 | 2 | 1.1 ± 0.1 | 1.3 ± 0.4 | 1.2 |
| | 3 | 3.3 ± 0.2 | 3.5 ± 0.3 | 1.1 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

This application claims priority to AT 1872/98 filed Nov. 10, 1998, the entirety of which is hereby incorporated by reference.

What is claimed is:

1. A pharmaceutical preparation comprising:

(A) a modified human Factor VIII polypeptide that has Factor VIII activity, wherein the modified human Factor VIII polypeptide differs from the human Factor VIII by at least one modification in at least one exosite of the A3 domain of said Factor VIII polypeptide, wherein said exosite is a hydrophilic moiety of the A3 domain of said modified human Factor VIII, and wherein the exosite is selected from the group of exosites, based upon the amino acid sequence of human Factor VIII polypeptide, consisting of the regions in said Factor VIII polypeptide: (i) 1743 (Phe) to 1749 (Arg), (ii) 1784 (Ser) to 1831 (Asp), (iii) 1886 (Ser) to 1919 (His), (iv) 1942 (Trp) to 1947 (Met), and (v) 1959 (Ser) to 1974 (Ala), wherein the modification is an amino acid substitution, deletion or insertion, and wherein the modification reduces the binding affinity to low-density lipoprotein receptor-related protein (LRP); and (B) an added lipoprotein receptor-related protein antagonist.

2. The preparation according to claim 1, wherein the lipoprotein receptor-related protein antagonists are selected from the group consisting of receptor-associated protein (RAP) and a fragment of lipoprotein receptor-related protein from clusters I, II, III or IV, wherein the fragment binds to a Factor VIII-LRP binding region.

3. The preparation according to claim 1, wherein the modified human Factor VIII polypeptide further comprises at least one modification in at least one exosite of the C2 domain, wherein exosite is a hydrophilic moiety of the C2 domain, and wherein the exosite is selected from the group of exosites, based upon the amino acid sequence of human Factor VIII polypeptide, consisting of amino acid regions (i) 2209 (Arg) to 2234 (Phe) and (ii) 2269 (His) to 2281 (Lys), wherein the modification is an amino acid substitution, deletion or insertion.

4. The preparation of claim 1, wherein the modified human Factor VIII polypeptide is produced by recombinant techniques.

5. A pharmaceutical preparation comprising:

(A) a modified human Factor VIII polypeptide that has Factor VIII activity, wherein the modified human Factor VIII polypeptide differs from the human Factor VIII by at least one modification in at least one exosite of the C1 domain, wherein said exosite is a hydrophilic moiety of the C1 domain, and wherein the exosite is selected from the group of exosites, based upon the amino acid sequence of human Factor VIII polypeptide, consisting of the regions in said Factor VIII polypeptide: (i) 2037 (Ile) to 2062 (Trp), (ii) 2108 (Asp) to 2118 (Asn), and (iii) 2154 (Thr) to 2158 (Ile), wherein the modification is an amino acid substitution, deletion or insertion, and wherein the modification reduces the binding affinity to low-density lipoprotein receptor-related protein (LRP); and (B) an added lipoprotein receptor-related protein antagonist.

6. The preparation according to claim 5, wherein the lipoprotein receptor-related protein antagonists are selected from the group consisting of receptor-associated protein (RAP) and a fragment of lipoprotein receptor-related protein from clusters I, II, III or IV, wherein the fragment binds to a Factor VIII-LRP binding region.

7. The preparation according to claim 5, wherein the modified human Factor VIII polypeptide further comprises at least one modification in at least one exosite of the C2 domain, wherein exosite is a hydrophilic moiety of the C2 domain, and wherein the exosite is selected from the group of exosites, based upon the amino acid sequence of human Factor VIII polypeptide, consisting of amino acid regions (i) 2209 (Arg) to 2234 (Phe) and (ii) 2269 (His) to 2281 (Lys), wherein the modification is an amino acid substitution, deletion or insertion.

8. The preparation of claim 5, wherein the modified human Factor VIII polypeptide is produced by recombinant techniques.

* * * * *

SEQUENCE LISTING

```
<160> NUMBER OF SEQ ID NOS: 14

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 1

ttaggatcca ccactatgca aatagagctc tcc                                33


<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 2

agtagtacga gttatttcac taaagcagaa tcgc                               34


<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 3

ttgcgattct gctttagtga aataactcgt actac                              35


<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 4

attgcggccg ctcagtagag gtcctgtgcc tc                                 32


<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 5

aatgcggccg cttcaattta aatcacagcc cat                                33
```

-continued

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ccggagatta ttacgaggac agttatgaag ac 32

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
gtcttcataa ctgtcctcgt aataatct 28

<210> SEQ ID NO 8
<211> LENGTH: 83
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
cgaattcacc cccagatttg ggaacaccag attgccctga ggctggagat tctgggctgc 60
gaggcacagc agcagtactg agc 83

<210> SEQ ID NO 9
<211> LENGTH: 85
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
ggccgctcag tactgctgct gtgcctcgca gcccagaatc tccagcctca gggcaatctg 60
gtgttcccaa atctgggggt gaatt 85

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
ctagaaccac cgttagtggc tcgctacgtg cgactgcacc cccagagttg ggctcaccat 60

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
attgccctga ggctggaggt tctgggctgc gatactcagc agccagcttg agc 53

-continued

```
<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12

ggccgctcaa gctggctgct gagtatcgca gc                                32


<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13

ccagaacctc cagcctcagg gcaatatggt gagcccaact ctgggggtgc                50


<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14

agtcgcacgt agcgagccac taacggtggt t                                 31
```